(12) United States Patent
Moriconi et al.

(10) Patent No.: US 8,133,911 B2
(45) Date of Patent: Mar. 13, 2012

(54) (R)-4-(HETEROARYL) PHENYLETHYL DERIVATIVES AND PHARMACEUTICAL COMPOSITIONS CONTAINING THEM

(75) Inventors: Alessio Moriconi, L'Aquila AQ (IT); Andrea Aramini, L'Aquila AQ (IT)

(73) Assignee: Dompe S.p.A (IT)

( * ) Notice: Subject to any disclaimer, the term of this patent is extended or adjusted under 35 U.S.C. 154(b) by 0 days.

(21) Appl. No.: 12/681,841

(22) PCT Filed: Oct. 17, 2008

(86) PCT No.: PCT/EP2008/064023
§ 371 (c)(1),
(2), (4) Date: Apr. 6, 2010

(87) PCT Pub. No.: WO2009/050258
PCT Pub. Date: Apr. 23, 2009

(65) Prior Publication Data
US 2010/0249198 A1 Sep. 30, 2010

(30) Foreign Application Priority Data
Oct. 18, 2007 (EP) .................................. 07020396

(51) Int. Cl.
| A61K 31/4174 | (2006.01) |
| A61K 31/422 | (2006.01) |
| A61K 31/427 | (2006.01) |
| C07D 233/88 | (2006.01) |
| C07D 263/48 | (2006.01) |
| C07D 277/38 | (2006.01) |

(52) U.S. Cl. ..... 514/370; 548/190; 548/233; 548/326.5; 514/377; 514/398

(58) Field of Classification Search ............... 548/190, 548/233, 326.5; 514/370, 377, 398
See application file for complete search history.

(56) References Cited

FOREIGN PATENT DOCUMENTS
| WO | WO 2007/060215 | 5/2007 |
| WO | WO-2007/060215 | * 5/2007 |

OTHER PUBLICATIONS

Amsterdam et al., "Limitation of reperfusion injury by a monoclonal antibody to C5a during myocardial infarction in pigs," The American Physiological Society, pp. H448-H457, 1995.

Arumugam et al., "Protective Effect of a New C5a Receptor Antagonist against Ischemia-Reperfusion Injury in the Rat Small Intestine," Journal of Surgical Research, 103, pp. 260-267, 2002.
Arumugam et al., "A small molecule C5a receptor antagonist protects kidneys from ischemia/reperfusion injury in rats," Kidney International, 63, pp. 134-142, 2003.
Arumugam et al., "Protective effect of a human C5a receptor antagonist against hepatic ischaemia-reperfusion injury in rats," Journal of Hepatoogy, 40, pp. 934-941, 2004.
Heller et al., "Selection of a C5a Receptor Antagonist from Phage Libraries Attenuating the Inflammatory Response in Immune Complex Disease and Ischemia/Reperfusion Injury,"The Journal of Immunology, 163. pp. 985-994, 1999.
Proctor et al., "Comparative Anti-Flammatory Activities of Antagonists to C3a and C5a Receptors in a Rat Model of Intestinal Ischaemia/Reperfusion Injury," British Journal of Pharmacology, 142, pp. 756-764, 2004.
Riedemann et al., "Complement in Ischemia Reperfusion Injury," American Journal of Pathology, 162(2), pp. 363-367, 2003.
Woodruff et al., "Protective Effects of a Potent C5a Receptor Antagonist on Experimental Acute Limb Ischemia-Reperfusion in Rats," Journal of Surgical Research, 116, pp. 81-90, 2004.
Vakeva et al., "Myocardial Infarction and Apoptosis After Myocardial Ischemia and Reperfusion: Role of the Terminal Complement Components and Inhibition by Anti-C5 Therapy," Circulation, 97, pp. 2259-2267, 1998.

\* cited by examiner

*Primary Examiner* — Kamal Saeed
*Assistant Examiner* — Janet L Coppins
(74) *Attorney, Agent, or Firm* — Jonathan D. Ball; King & Spalding LLP

(57) ABSTRACT

The present invention relates to a novel class of (R)-4-(heteroaryl)phenylpropionic derivatives of formula (I), useful in the inhibition of the chemotactic activation induced by the fraction C5a of complement. Said compounds are useful in the treatment of pathologies depending on the chemotactic activation of neutrophils and monocytes induced by the fraction C5a of the complement. In particular, the compounds of the invention are useful in the treatment of autoimmune hemolytic anemia (AIHA), psoriasis, bullous pemphigoid, rheumatoid arthritis, ulcerative colitis, acute respiratory distress syndrome, idiopathic fibrosis, glomerulonephritis and in the prevention and treatment of injury caused by ischemia and reperfusion.

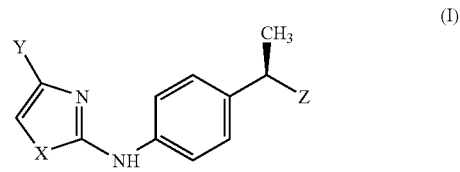

10 Claims, No Drawings

(R)-4-(HETEROARYL) PHENYLETHYL DERIVATIVES AND PHARMACEUTICAL COMPOSITIONS CONTAINING THEM

FIELD OF THE INVENTION

The present invention relates to a novel class of (R)-4-(heteroaryl)phenylpropionic derivatives useful in the inhibition of the chemotactic activation induced by the fraction C5a of complement. Said compounds are useful in the treatment of pathologies depending on the chemotactic activation of neutrophils and monocytes induced by the fraction C5a of the complement. In particular, the compounds of the invention are useful in the treatment of autoimmune hemolytic anemia (AIHA), psoriasis, bullous pemphigoid, rheumatoid arthritis, ulcerative colitis, acute respiratory distress syndrome, idiopathic fibrosis, glomerulonephritis and in the prevention and treatment of injury caused by ischemia and reperfusion.

STATE OF THE ART

In response to immunologic and infective events, activation of the complement system mediates amplification of inflammatory response both via direct membrane action and via release of a series of peptide fragments, generally known as anaphylatoxins, generated by enzymatic cleavage of the C3, C4 and C5 complement fractions. These peptides include C3a and C4a, both of 77 aminoacids; in turn, C5 convertase cleaves the C5 complement fraction to give the glycoprotein C5a of 74 aminoacids.

The C5a peptide fragment of the complement has been defined as the "complete" pro-inflammatory mediator due to its chemotactic and inflammatory activity. In fact, other inflammatory mediators such as selected chemokines (IL-8, MCP-1 and RANTES, for example) are highly selective towards self-attracted cells, while others, such as histamine and bradykinin, are only weak chemotactic agents.

Convincing evidences support the involvement of C5a, in vivo, in several pathological conditions including ischemia/reperfusion, autoimmune dermatitis, membrane-proliferative idiopathic glomerulonephritis, airway irresponsiveness and chronic inflammatory diseases, ARDS and CODP, Alzheimer's disease, juvenile rheumatoid arthritis (N. P. Gerard, Ann. Rev. Immunol., 12, 755, 1994).

Specifically, the presence of elevated anaphylotoxin C3a and C5a levels is but one of several indications that the complement system is hyperactive in rheumatoid arthritis (RA) patients. A recently published paper (E. P. Grant, J. Exp. Med., 196(11), 1461, 2002) reports that genetic deletion of C5aR completely protects mice from arthritis induced with anti collagen antibodies, indicating a central role for C5a-dependent cell recruitment and activation in the initial phase of arthritis. These data raise the possibility that novel drugs and biotherapeutics targeting C5aR may provide new strategies for therapeutic intervention to block the effector phase of RA.

The pathological significance of C5a and C5aR in the development of diseases related to antibody-dependent type II autoimmunity has been also investigated, specifically in the insurgence of autoimmune haemolytic anaemia (AIHA), a disease characterized by the production of antibodies directed against self red blood cells (RBCs) that causes haemolysis. AIHA is a fairly uncommon disorder, with estimates of incidence at 1-3 cases/100,000/year. A crucial role of C5a in IgG-dependent AIHA, independent from the chemotactic function of this anaphylotoxin, has been identified in experimental animal models (V. Kumar, J. Clin. Invest., 116(2), 512, 2006). In fact, it has been observed that mice lacking C5aR are partially resistant to this IgG autoantibody-induced disease model and a cross-talk of C5aR with activating Fcγ receptors, specifically on liver macrophages, has been identified through the observation that, upon administration of anti-erythrocyte antibodies, upregulation of activating FcγRs on Kupfer cells was absent in C5aR-deficient mice; parallely, in mice deficient in FcγRs, C5 and C5a production was abolished. This is the first evidence of a previously unidentified FcγR-mediated C5a-generating pathway, suggesting the role of C5a in the development of antibody-dependent autoimmune diseases and potential therapeutic benefits of C5a and/or C5aR blockade in AIHA related to type II autoimmune injury.

The control of the synthesis of complement fractions is considered a promising therapeutic target in the treatment of shock and in the prevention of rejection during organ transplant (multiple organ failure and hyperacute graft rejection) (Issekutz A. C. et al., Int. J. Immunopharmacol, 12, 1, 1990; Inagi R. et at., Immunol. Lett., 27, 49, 1991). More recently, inhibition of complement fractions has been reported to be involved in the prevention of native and transplanted kidney injuries taking account of complement involvement in the pathogenesis of both chronic interstitial and acute glomerular renal injuries. (Sheerin N. S. & Sacks S. H., Curr. Opinion Nephrol. Hypert., 7, 395, 1998).

Characteristic neutrophil accumulation occurs in acute and chronic pathologic conditions, for example in the highly inflamed and therapeutically recalcitrant areas of psoriatic lesions. Neutrophils are chemotactically attracted and activated by the synergistic action of chemokines, like CXCL8 and GRO-α, released by the stimulated keratinocytes, and of the C5a/C5a-desArg fraction produced through the alternative complement pathway activation (T. Terui et al., Exp. Dermatol., 9, 1, 2000). We described a novel class of "omega-aminoalkylamides of R-2-aryl-propionic acids" as inhibitors of the chemotaxis of polymorphonucleate and mononucleate cells" (WO 02/068377). Furthermore, quaternary ammonium salts of omega-aminoalkylamides of (R)-2-arylpropionic acids were reported as selective inhibitors of C5a-induced neutrophils and monocytes chemotaxis (WO 03/029187). More recently, we described novel (R)-arylalkylamino derivatives (PCT/EP2006/068867) as potent and selective inhibitors of C5-induced human PMN chemotaxis, belonging to the chemical classes of sulfonamides and amides.

DETAILED DESCRIPTION OF THE INVENTION

Surprisingly, we have now found a novel class of (R)-4-(heteroaryl)phenylpropionic derivatives with strong selectivity and potency in inhibiting C5a induced neutrophil chemotaxis. The novel compounds are inactive in the COXs inhibition in a concentration range between $10^{-5}$ and $10^{-6}$M.

The novel compounds are substituted or unsubstituted tetrazoles, hydroxyazoles, thiadiazoles, pyrazoles and triazoles.

The present invention relates to novel compounds useful in the inhibition of the chemotactic activation induced by the fraction C5a of complement. Said compounds are useful in the treatment of pathologies depending on the chemotactic activation of neutrophils and monocytes induced by the fraction C5a of the complement. In particular, the compounds of the invention are useful in the treatment of autoimmune hemolytic anemia (AIHA) and rheumatoid arthritis. Moreover, they are also useful in the treatment of psoriasis, bullous pemphigoid, ulcerative colitis, acute respiratory distress syndrome, idiopathic fibrosis, glomerulonephritis and in the prevention of injury caused by ischemia and reperfusion.

The present invention relates to compounds of formula (I):

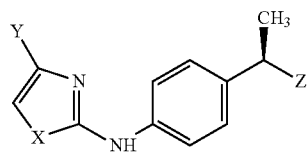

and pharmaceutically acceptable salts thereof,
wherein
X is a heteroatom selected from
S, O and N
Y is H or a residue selected from
halogen, linear or branched $C_1$-$C_4$-alkyl, $C_2$-$C_4$-alkenyl, $C_1$-$C_4$-alkoxy, hydroxy, —COOH, $C_1$-$C_4$-acyloxy, phenoxy, cyano, nitro, $NH_2$, $C_1$-$C_4$-acylamino, halo-$C_1$-$C_3$-alkyl, benzoyl, linear or branched $C_1$-$C_8$-alkanesulfonate, linear or branched $C_1$-$C_8$-alkanesulfonamides, linear or branched $C_1$-$C_8$-alkyl sulfonylmethyl;
Z is an heteroaryl ring selected from
unsubstituted tetrazole and
triazole, pyrazole, oxazole, thiazole, isooxazole, isothiazole, thiadiazole and oxadiazole substituted by one hydroxy group and optionally further substituted by one or more groups selected from the group consisting of halogen, linear or branched $C_1$-$C_4$-alkyl, $C_2$-$C_4$-alkenyl, $C_1$-$C_4$-alkylamino, $C_1$-$C_4$-alkoxy, $C_1$-$C_4$-alkylthio, $C_1$-$C_4$-acyloxy, cyano, nitro, $NH_2$, $C_1$-$C_4$-acylamino, halo-$C_1$-$C_3$-alkyl, halo-$C_1$-$C_3$-alkoxy, linear or branched $C_1$-$C_8$-alkanesulfonate and linear or branched $C_1$-$C_8$-alkanesulfonamides.

According to a preferred embodiment of the invention the compounds of formula I are those wherein:
X is a heteroatom selected from
S and O
Y is H or a residue selected from
halogen, linear or branched $C_1$-$C_4$-alkyl and halo-$C_1$-$C_3$-alkyl;
Z is an heteroaryl ring selected from the group consisting of:
unsubstituted tetrazole and
triazole, pyrazole, isooxazole, isothiazole, thiadiazole and oxadiazole substituted by one hydroxy group and optionally further substituted by one or more groups selected from the group consisting of halogen, linear or branched $C_1$-$C_4$-alkyl, $C_1$-$C_4$-alkylthio and halo-$C_1$-$C_3$-alkyl.

Particularly preferred, among the above compounds of formula I, are those wherein
Y is H or selected from the group consisting of trifluoromethyl, chlorine, methyl and tert-butyl
and/or wherein said triazole, pyrazole, isooxazole, isothiazole, thiadiazole or oxadiazole ring is substituted by one hydroxy group and optionally further substituted by one or more groups selected from the group consisting of methyl, trifluoromethyl and chlorine.

Particularly preferred compounds of formula (I) are:
1—N-{4-[(1R)-1-(1H-tetrazol-5-yl)ethyl]phenyl}-4-(trifluoromethyl)-1,3-thiazol-2-amine;
2—4-methyl-N-{4-[(1R)-1-(1H-tetrazol-5-yl)ethyl]phenyl}-1,3-thiazol-2-amine;
3—4-tert-butyl-N-{4-[(1R)-1-(1H-tetrazol-5-yl)ethyl]phenyl}-1,3-thiazol-2-amine;
4—N-{4-[(1R)-1-(1H-tetrazol-5-yl)ethyl]phenyl}-1,3-thiazol-2-amine;
5—N-{4-[(1R)-1-(1H-tetrazol-5-yl)ethyl]phenyl}-4-(trifluoromethyl)-1,3-oxazol-2-amine;
6—4-methyl-N-{4-[(1R)-1-(1H-tetrazol-5-yl)ethyl]phenyl}-1,3-oxazol-2-amine;
7—5-[(1R)-1-(4-{[4-(trifluoromethyl)-1,3-thiazol-2-yl]amino}phenyl)ethyl]-1H-pyrazol-1-ol;
8—4-methyl-5-[(1R)-1-(4-{[4-(trifluoromethyl)-1,3-thiazol-2-yl]amino}phenyl)ethyl]-1H-pyrazol-1-ol;
9—5-[(1R)-1-(4-{[4-(trifluoromethyl)-1,3-thiazol-2-yl]amino}phenyl)ethyl]-1H-1,2,3-triazol-1-ol;
10—5-[(1R)-1-(4-{[4-(trifluoromethyl)-1,3-thiazol-2-yl]amino}phenyl)ethyl]isoxazol-3-ol;
11—4-methyl-5-[(1R)-1-(4-{[4-(trifluoromethyl)-1,3-thiazol-2-yl]amino}phenyl)ethyl]isoxazol-3-ol;
12—5-[(1R)-1-(4-{[4-(trifluoromethyl)-1,3-thiazol-2-yl]amino}phenyl)ethyl]isothiazol-3-ol;
13—4-[(1R)-1-(4-{[4-(trifluoromethyl)-1,3-thiazol-2-yl]amino}phenyl)ethyl]-1,2,5-oxadiazol-3-ol;
14—4-[(1R)-1-(4-{[4-(trifluoromethyl)-1,3-thiazol-2-yl]amino}phenyl)ethyl]-1,2,5-thiadiazol-3-ol;
15—5-[(1R)-1-(4-{[4-(trifluoromethyl)-1,3-thiazol-2-yl]amino}phenyl)ethyl]-1H-1,2,4-triazol-1-ol.

The preferred compounds are those in which the substituent in 4-position of the phenyl ring is a substituted or unsubstituted 2-aminothiazole moiety.

The most preferred compound in the list is the compound 1 [N-{4-[(1R)-1-(1H-tetrazol-5-yl)ethyl]phenyl}-4-(trifluoromethyl)-1,3-thiazol-2-amine].

As will be demonstrated in the Experimental section that follows, the compounds of formula (I) are potent inhibitors of the human PMNs chemotaxis induced by C5a.

It is therefore a further object of the present invention to provide compounds of formula (I) for use in the treatment of diseases that involve C5a induced human PMNs chemotaxis.

Furthermore, it has also surprisingly been found that the compounds of formula (I) do not interfere with the production of $PGE_2$ induced in murine macrophages by lipopolysaccharides stimulation (LPS, 1 µg/ml) at a concentration ranging between $10^{-5}$ and $10^{-7}$ M.

It is therefore a further object of the present invention the use of the compounds of the invention as medicaments.

In view of the experimental evidences discussed above and of the role performed by the complement cascade, and namely its fraction C5a, in the processes that involve the activation and the infiltration of neutrophils, the compounds of the invention are particularly useful in the treatment of diseases such as autoimmune haemolytic anaemia (AIHA), rheumatoid arthritis (M. Selz et al., J. Clin. Invest., 87, 463, 1981), psoriasis (R. J. Nicholoff et al., Am. J. Pathol., 138, 129, 1991), bullous pemphigoid, intestinal chronic inflammatory pathologies such as ulcerative colitis (Y. R. Mahida et al., Clin. Sci., 82, 273, 1992), acute respiratory distress syndrome and idiopathic fibrosis (E. J. Miller, previously cited, and P. C. Carré et al., J. Clin. Invest., 88, 1882, 1991), cystic fibrosis, glomerulonephritis (T. Wada et al., J. Exp. Med., 180, 1135, 1994) and in the prevention and the treatment of injury caused by ischemia and reperfusion.

It is then a further object of the invention to provide compounds of formula (I) for use in the treatment of autoimmune hemolytic anemia (AIHA), psoriasis, bullous pemphigoid, rheumatoid arthritis, ulcerative colitis, acute respiratory distress syndrome, idiopathic fibrosis, glomerulonephritis and in the prevention and treatment of injury caused by ischemia and reperfusion.

To this purpose, the compounds of the invention of formula (I) are conveniently formulated in pharmaceutical compositions using conventional techniques and pharmaceutically acceptable excipients and/or diluents such as those described in "Remington's Pharmaceutical Sciences Handbook" MACK Publishing, New York, 18th ed., 1990.

The compounds of the invention can be administered by intravenous injection, as a bolus, in dermatological preparations (creams, lotions, sprays and ointments), by inhalation as well as orally in the form of capsules, tablets, syrup, controlled-release formulations and the like.

The average daily dose depends on several factors such as the severity of the disease, the condition, age, sex and weight of the patient. The dose will vary generally from 1 to 1500 mg of compounds of formula (I) per day, optionally divided in multiple administrations.

Different experimental procedures have been followed for the synthesis of compounds of formula (I). As far as it concerns tetrazoles, exemplified in the examples 1-6, they were synthesised by a common procedure started from the related carboxylic acid. The acids were transformed into the corresponding primary amides by standard procedures of treatment with coupling agents, like 1,1'-carbonyldiimidazole, and following reaction with ammonia. The conversion of the amide into nitrile by dehydratation, followed by treatment of the nitrile of formula

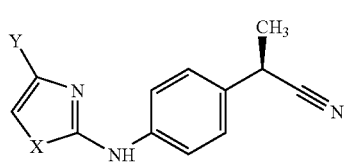

(II)

wherein
X is a heteroatom selected from
—S, O and N
Y is H or a residue selected from
halogen, linear or branched $C_1$-$C_4$-alkyl, $C_2$-$C_4$-alkenyl, $C_1$-$C_4$-alkoxy, hydroxy, —COOH, $C_1$-$C_4$-acyloxy, phenoxy, cyano, nitro, —$NH_2$, $C_1$-$C_4$-acylamino, halo-$C_1$-$C_3$-alkyl, benzoyl, linear or branched $C_1$-$C_8$-alkanesulfonate, linear or branched $C_1$-$C_8$-alkanesulfonamides, linear or branched $C_1$-$C_8$-alkyl sulfonylmethyl;
by trimethylsilylazide, afforded the desired tetrazoles. The performed experimental procedures both for tetrazoles and for the other heteroaryl derivatives 7-15 were derived from published procedures, adapted to the specific substrates of the invention (Friederick K. et al. in Rapoport Z., The Chemistry of the Cyano Group, Wiley, N.Y., 96, 1970; Matzen L. et al., Sisido K. et al., J. Organomet. Chem., 33, 337, 1971; J. Med. Chem., 40, 520, 1997; StensbØl T. B. et al., J. Med. Chem., 45, 19, 2002; Lolli M. L. et al., J, Med. Chem., 49, 4442, 2006).

The following examples illustrate the invention.

EXPERIMENTAL SECTION

List of Abbreviations $CH_2Cl_2$: dichloromethane; $CH_3CN$: acetonitrile; $CHCl_3$: chloroform; HCl: hydrochloric acid; $CH_3OH$: methanol; AcOH: acetic acid; EtOAc: ethyl acetate; DIBAH: diisobutylaluminum hydride; $Et_2O$: diethyl ether; EtOH: ethanol; m-CPBA: meta-chloroperbenzoic acid; CDI: 1,1'-carbonyldiimidazole.

EXAMPLE 1

Preparation of Intermediates

Methyl (2R)-2-[4-(carbamothioylamino)phenyl]propanoate

A solution of (2R)-2-(4-nitrophenyl)propanoic acid (25 g, 0.128 mol) in $CH_3OH$ (120 ml) was treated at room temperature with 37% HCl (5 ml) and refluxed for 4 h. The solvent was removed under vacuum and the crude methyl ester intermediate was used for the further step.

Iron powder (71 g, 1.28 mol) was suspended in a mixture of $CH_3OH$ (250 ml) and water (20 ml); the mixture was heated, treated with 37% HCl (0.5 ml), then refluxed for 1 h. After cooling at room temperature a solution of the crude methyl ester in $CH_3OH$ (25 ml) was added dropwise in 30 min. and the resulting solution was refluxed overnight. The suspension was filtered still hot on a celite short path column and the filtrate evaporated to afford an orange oil (20 g) that was diluted with $CH_2Cl_2$ (200 cc) and extracted with a saturated $NaHCO_3$ aqueous solution (3×150 ml), dried over anhydrous $Na_2SO_4$ and evaporated under vacuum to give the pure methyl (2R)-2-(4-aminophenyl)propanoate (17.5 g, 98 mmol) as orange oil (76%). $^1$H-NMR ($CDCl_3$): δ 7.05 (d, 2H, J=7 Hz), 6.65 (d, 2H, J=7 Hz), 3.80 (m, 1H), 3.75 (bs, 2H, $NH_2$), 3.60 (s, 3H), 1.45 (d, 3H, J=7 Hz).

To a solution of the methyl ester (17.5 g, 98 mmol) in toluene (300 ml) conc. $H_2SO_4$ (2.6 ml, 0.05 mol) was slowly added. Then sodium thiocyanate (10.29 g, 0.128 mol) was added to the suspension and the reaction mixture refluxed for 24 h. After cooling at room temperature, the mixture was washed with a saturated aqueous solution of $NH_4Cl$ (2×100 ml), dried over anhydrous $Na_2SO_4$ and evaporated under vacuum to give a crude that, after purification by flash chromatography (n-hexane/EtOAc 1:1) afforded the methyl (2R)-2-[4-(carbamothioylamino)phenyl]propanoate (10.7 g, 48.4 mmol) as white solid (49%). $^1$H-NMR ($CDCl_3$): δ 8.25 (bs, 1H, CSNH), 7.40 (d, 2H, J=7 Hz), 7.20 (d, 2H, J=7 Hz), 6.20 (bs, 2H, $CSNH_2$), 3.75 (m, 1H), 3.65 (s, 3H), 1.50 (d, 3H, J=7 Hz).

(2R)-2-(4-{[4-(trifluoromethyl)-1,3-thiazol-2-yl]amino}phenyl)propanoic acid

A solution of methyl (2R)-2-[4-(carbamothioylamino)phenyl]propanoate (10.7 g, 0.0484 mol) in dioxane (200 ml) was treated at room temperature with 3-bromo-1,1,1-trifluoro-propan-2-one (5 ml, 0.0484 mol) and the resulting mixture was refluxed for 2 h. After cooling at room temperature, the solvent was evaporated under vacuum, the crude diluted with $CH_2Cl_2$ (200 ml) and washed with a saturated $NaHCO_3$ aqueous solution (3×100 ml), dried over anhydrous $Na_2SO_4$ and evaporated to give pure methyl (2R)-2-(4-{[4-(trifluoromethyl)-1,3-thiazol-2-yl]amino}phenyl)propanoate (12.8 g, 38.7 mmol) as yellow oil (80%). $^1$H-NMR ($CDCl_3$): δ 8.65 (bs, 1H, NH), 7.30 (m, 4H), 7.05 (s, 1H), 3.75 (q, 1H, J=7 Hz), 3.65 (s, 3H), 1.50 (d, 3H, J=7 Hz).

A solution of the methyl ester (12.8 g, 38.7 mmol) in AcOH (50 ml) and 37% HCl (17.5 ml) was refluxed for 12 h. After cooling at room temperature and solvents evaporation, the crude was diluted in $CH_2Cl_2$ (200 ml) and washed with water (3×100 ml) and brine (3×100 ml). The organic layer was dried over anhydrous $Na_2SO_4$ and the solvent evaporated to give a pale yellow oil that, after pulping in n-hexane overnight, afforded pure (2R)-2-(4-{[4-(trifluoromethyl)-1,3-thiazol-2-yl]amino}phenyl)propanoic acid (8.4 g, 26 mmol) as a white solid (68%). $^1$H-NMR ($CDCl_3$): δ 9.25 (bs, 1H, NH), 7.40 (d, 2H, J=7 Hz), 7.25 (d, 2H, J=7 Hz), 7.00 (s, 1H), 3.80 (q, 1H, J=7 Hz), 1.55 (d, 3H, J=7 Hz).

(2R)-2-{4-[(4-methyl-1,3-thiazol-2-yl)amino] phenyl}propanoic acid

The acid was obtained following the same procedure described for (2R)-2-(4-{[4-(trifluoromethyl)-1,3-thiazol-2-yl]amino}phenyl)propanoic acid and starting from methyl (2R)-2-[4-(carbamothioylamino)phenyl]propanoate (2.0 g, 8.40 mmol) and chloro-2-propanone (0.67 ml, 8.40 mmol). The following acid hydrolysis afforded the pure (2R)-2-{4-[(4-methyl-1,3-thiazol-2-yl)amino]phenyl}propanoic acid (1.65 g, 6.30 mol) as a yellow oil (75%). $^1$H-NMR ($CDCl_3$): δ 8.15 (bs, 1H, NH), 7.40 (d, 2H, J=7 Hz), 7.20 (d, 2H, J=7 Hz), 6.35 (s, 1H), 3.75 (q, 1H, J=7 Hz), 2.18, (s, 3H), 1.50 (d, 3H, J=7 Hz).

(2R)-2-{4-[(4-tert-butyl-1,3-thiazol-2-yl)amino] phenyl}propanoic acid

The acid was obtained following the same procedure described for (2R)-2-(4-{[4-(trifluoromethyl)-1,3-thiazol-2-yl]amino}phenyl)propanoic acid and starting from methyl (2R)-2-[4-(carbamothioylamino)phenyl]propanoate (2.0 g, 8.40 mmol) and 1-bromopinacolone (1.13 ml, 8.40 mmol). The following acid hydrolysis afforded the pure (2R)-2-{4-[(4-tert-butyl-1,3-thiazol-2-yl)amino]phenyl}propanoic acid (1.41 g, 4.62 mmol) as pale yellow oil (55%). $^1$H-NMR ($CDCl_3$): δ 8.30 (bs, 1H, NH), 7.40 (d, 2H, J=7 Hz), 7.20 (d, 2H, J=7 Hz), 6.40 (s, 1H), 3.75 (q, 1H, J=7 Hz), 1.50 (d, 3H, J=7 Hz), 1.40, (s, 9H).

(2R)-2-[4-(1,3-thiazol-2-ylamino)phenyl]propanoic acid

The acid was obtained following the same procedure described for (2R)-2-(4-{[4-(trifluoromethyl)-1,3-thiazol-2-yl]amino}phenyl)propanoic acid and starting from methyl (2R)-2-[4-(carbamothioylamino)phenyl]propanoate (2.0 g, 8.40 mmol) and chloroacetaldehyde (50 wt. % in $H_2O$, 0.54 ml, 8.40 mmol). The following acid hydrolysis afforded the pure (2R)-2-{4-[(1,3-thiazol-2-yl)amino]phenyl}propanoic acid (1.47 g, 5.62 mmol) as pale yellow oil (55%). $^1$H-NMR ($CDCl_3$): δ 8.30 (bs, 1H, NH), 8.10 (d, 1H, J=2.5 Hz), 7.50 (d, 1H, J=2.5 Hz) 7.40 (d, 2H, J=7 Hz), 7.20 (d, 2H, J=7 Hz), 3.75 (q, 1H, J=7 Hz), 1.50 (d, 3H, J=7 Hz),

Methyl (2R)-2-[4-(carbamoylamino)phenyl]propanoate

To a solution of methyl (2R)-2-(4-aminophenyl)propanoate (3.0 g, 18.1 mmol) in toluene (50 ml) conc. $H_2SO_4$ (0.47 ml, 50 mmol) was slowly added. Then sodium cyanate (1.88 g, 28 mmol) was added to the suspension and the reaction mixture refluxed for 24 h. After cooling at room temperature, the mixture was washed with a saturated aqueous solution of $NH_4Cl$ (2×30 ml), dried over anhydrous $Na_2SO_4$ and evaporated under vacuum to give a crude that, after purification by flash chromatography (n-hexane/EtOAc 1:1) afforded the methyl (2R)-2-[4-(carbamoylamino)phenyl]propanoate (2.07 g, 9.95 mmol) as white solid (55%). $^1$H-NMR ($CDCl_3$): δ 9.35 (bs, 1H, CONH), 7.45 (d, 2H, J=7 Hz), 7.25 (d, 2H, J=7 Hz), 6.55 (bs, 2H, $CONH_2$), 3.75 (m, 1H), 1.50 (d, 3H, J=7 Hz).

(2R)-2-(4-{[4-(trifluoromethyl)-1,3-oxazol-2-yl] amino}phenyl)propanoic acid A solution of methyl (2R)-2-[4-(carbamoylamino)phenyl] propanoate (2.7 g, 9.95 mmol) in dioxane (50 ml) was treated at room temperature with 3-bromo-1,1,1-trifluoro-propan-2-one (1.03 ml, 10 mmol) and the resulting mixture was refluxed for 2 h. After cooling at room temperature, the solvent was evaporated under vacuum, the crude diluted with $CH_2Cl_2$ (50 ml) and washed with a saturated $NaHCO_3$ aqueous solution (3×30 ml), dried over anhydrous $Na_2SO_4$ and evaporated to give pure methyl (2R)-2-(4-{[4-(trifluoromethyl)-1,3-oxazol-2-yl]amino}phenyl)propanoate (2.5 g, 7.96 mmol) as yellow oil (80%). $^1$H-NMR ($CDCl_3$): δ 10.05 (bs, 1H, NH), 8.30 (s, 1H), 7.45 (d, 2H, J=7 Hz), 7.25 (d, 2H, J=7 Hz), 3.75 (q, 1H, J=7 Hz), 3.65 (s, 3H), 1.50 (d, 3H, J=7 Hz).

A solution of the methyl ester (2.5 g, 7.96 mmol) in AcOH (4.1 ml) and 37% HCl (1.42 ml) was refluxed for 12 h. After cooling at room temperature and solvents evaporation, the crude was diluted in $CH_2Cl_2$ (20 ml) and washed with water (3×15 ml) and brine (3×15 ml). The organic layer was dried over anhydrous $Na_2SO_4$ and the solvent evaporated to give a pale yellow oil that, after pulping in diethyl ether overnight, afforded pure (2R)-2-(4-{[4-(trifluoromethyl)-1,3-oxazol-2-yl]amino}phenyl)propanoic acid (1.86 g, 6.21 mmol) as a white solid (78%). $^1$H-NMR ($CDCl_3$): δ 9.25 (bs, 1H, NH), 7.40 (d, 2H, J=7 Hz), 7.25 (d, 2H, J=7 Hz), 7.00 (s, 1H), 3.80 (q, 1H, J=7 Hz), 1.55 (d, 3H, J=7 Hz).

(2R)-2-{4-[(4-methyl-1,3-oxazol-2-yl)amino] phenyl}propanoic acid

The acid was obtained following the same procedure described for (2R)-2-(4-{[4-(trifluoromethyl)-1,3-oxazol-2-yl]amino}phenyl)propanoic acid and starting from methyl (2R)-2-[4-(carbamoylamino)phenyl]propanoate (2.0 g, 9.95 mmol) and chloro-2-propanone (0.80 ml, 9.95 mmol). The following acid hydrolysis afforded the pure (2R)-2-{4-[(4-methyl-1,3-thiazol-2-yl)amino]phenyl}propanoic acid (1.71 g, 6.96 mol) as a yellow oil (70%). $^1$H-NMR ($CDCl_3$): δ 9.65 (bs, 1H, NH), 7.95 (s, 1H), 7.45 (d, 2H, J=7 Hz), 7.25 (d, 2H, J=7 Hz), 3.75 (q, 1H, J=7 Hz), 2.20 (s, 3H), 1.50 (d, 3H, J=7 Hz).

EXAMPLE 2

Synthesis of Compounds of Formula I

N-{4-[(1R)-1-(1H-tetrazol-5-yl)ethyl]phenyl}-4-(trifluoromethyl)-1,3-thiazol-2-amine (1)

1a) (2R)-2-(4-{[4-(trifluoromethyl)-1,3-thiazol-2-yl] amino}phenyl)propanamide

To a cooled mixture (0-5° C.) of (2R)-2-(4-{[4-(trifluoromethyl)-1,3-thiazol-2-yl]amino}phenyl)propanoic acid (1 g, 3.16 mmol) in $CH_2Cl_2$ (20 mL), 1,1-carbonyldiimidazole (CDI) (0.512 g, 3.16 mmol) was added. After stirring for 1 h at 0-5° C. gaseous ammonia was bubbled into the mixture for 4 h and then left stirring at room temperature until the complete disappearance of the starting material. The reaction was quenched adding a $H_3PO_4/H_2PO_4^-$ buffer solution (pH=2.0, 5 ml), the two phases were separated and the organic one washed with the same buffer (3×10 mL) and water (3×10 mL), dried over anhydrous $Na_2SO_4$ and evaporated under vacuum to give (2R)-2-(4-{[4-(trifluoromethyl)-1,3-thiazol-2-yl]amino}phenyl) propanamide (788 mg, 2.5 mmol) as a white solid (79%) used without further purification.

1b) (2R)-2-(4-{[4-(trifluoromethyl)-1,3-thiazol-2-yl]amino}phenyl)propanenitrile To a cooled (0-5° C.) solution of the amide in toluene (10 mL), a phosgene solution (1.93 M in toluene, 5.2 mL) was added dropwise. The resulting mixture was left stirring at room temperature overnight, then evaporated under vacuum and the crude diluted with $CH_2Cl_2$. The organic layer was washed with a saturated solution of $NaHCO_3$ (2×10 ml), with water (3×5 ml) and with brine (3×5 ml), dried over anhydrous $Na_2SO_4$ and, after solvent evaporation the intermediate (2R)-2-(4-{[4-(trifluoromethyl)-1,3-thiazol-2-yl]amino}phenyl) propanenitrile (639 mg, 2.15 mmol) was isolated as a colourless oil (86%) and used for the next step.

1c) N-{4-[(1R)-1-(1H-tetrazol-5-yl)ethyl]-phenyl}-4-(trifluoromethyl)-1,3-thiazol-2-amine Tetrabutylammonium fluoride trihydrate (339 mg, 1.075 mmol) and trimethylsilyl azide (0.342 mL, 2.58 mmol) were added to the nitrile intermediate (639 mg, 2.15 mmol). The resulting mixture was heated with vigorous stirring at 85° C. for 18 h. After cooling at room temperature, the crude mixture was diluted with EtOAc (20 ml) and washed with 1M HCl (3×5 mL), dried over anhydrous $Na_2SO_4$ and evaporated under reduced pressure to give the pure N-{4-[(1R)-1-(1H-tetrazol-5-yl)ethyl]phenyl}-4-(trifluoromethyl)-1,3-thiazol-2-amine (1) (329 mg, 0.97 mmol) as a brown solid (45%). $[\alpha]_D=-36$ (c=1; $CH_3OH$); $^1$H-NMR ($CD_3OD$): δ 9.45 (bs, 1H, NH), 7.45 (d, 2H, J=7 Hz), 7.30 (d, 2H, J=7 Hz), 7.15 (s, 1H), 3.95 (q, 1H, J=7 Hz), 1.65 (d, 3H, J=7 Hz).

4-Methyl-N-{4-[(1R)-1-(1H-tetrazol-5-yl)ethyl]phenyl}-1,3-thiazol-2-amine (2)

Compound 2 was obtained following the procedure described for the synthesis of 1 starting from the intermediate (2R)-2-{4-[(4-methyl-1,3-thiazol-2-yl)amino]phenyl}propanoic acid (4.1 mmol). Pure 4-methyl-N-{4-[(1R)-1-(1H-tetrazol-5-yl)ethyl]phenyl}-1,3-thiazol-2-amine (2) was isolated (0.65 g, 2.26 mmol) as a white solid (55%). $[\alpha]_D=-26$ (c=1; $CH_3OH$); $^1$H-NMR ($CD_3OD$): δ 8.20 (bs, 1H, NH), 7.45 (d, 2H, J=7 Hz), 7.30 (d, 2H, J=7 Hz), 6.25 (s, 1H), 3.95 (q, 1H, J=7 Hz), 2.20, (s, 3H), 1.55 (d, 3H, J=7 Hz).

4-tert-Butyl-N-{4-[(1R)-1-(1H-tetrazol-5-yl)ethyl]phenyl}-1,3-thiazol-2-amine (3)

Compound 3 was obtained following the procedure described for the synthesis of 1 starting from the intermediate (2R)-2-{4-[(4-tert-butyl-1,3-thiazol-2-yl)amino]phenyl}propanoic acid (3.5 mmol). Pure 4-tert-butyl-N-{4-[(1R)-1-(1H-tetrazol-5-yl)ethyl]phenyl}-1,3-thiazol-2-amine (3) was isolated (0.57 g, 1.75 mmol) as a white solid (50%). $[\alpha]_D=-46$ (c=1; $CH_3OH$); $^1$H-NMR ($CD_3OD$): δ 9.35 (bs, 1H, NH), 7.40 (m, 4H), 7.25 (s, 1H), 3.85 (q, 1H, J=7 Hz), 1.55 (d, 3H, J=7 Hz), 1.40, (s, 9H).

N-{4-[(1R)-1-(2H-tetrazol-5-yl)ethyl]phenyl}-1,3-thiazol-2-amine (4)

Compound 4 was obtained following the procedure described for the synthesis of 1 starting from the intermediate (2R)-2-{4-[(1,3-thiazol-2-yl)amino]phenyl}propanoic acid (3.5 mmol). Pure N-{4-[(1R)-1-(2H-tetrazol-5-yl)ethyl]phenyl}-1,3-thiazol-2-amine (4) was isolated (0.48 g, 1.75 mmol) as a white solid (50%). $[\alpha]_D=-45$ (c=1; $CH_3OH$); $^1$H-NMR ($CDCl_3$): δ 8.30 (bs, 1H, NH), 8.10 (d, 1H, J=2.5 Hz), 7.50 (d, 1H, J=2.5 Hz) 7.40 (d, 2H, J=7 Hz), 7.20 (d, 2H, J=7 Hz), 3.75 (q, 1H, J=7 Hz), 1.50 (d, 3H, J=7 Hz).

N-{4-[(1R)-1-(1H-tetrazol-5-yl)ethyl]phenyl}-4-(trifluoromethyl)-1,3-oxazol-2-amine (5)

Compound 5 was obtained following the procedure described for the synthesis of 1 starting from the intermediate (2R)-2-(4-{[4-(trifluoromethyl)-1,3-oxazol-2-yl]amino}phenyl)propanoic acid (3.5 mmol). Pure N-{4-[(1R)-1-(1H-tetrazol-5-yl)ethyl]phenyl}-4-(trifluoromethyl)-1,3-oxazol-2-amine (5) was isolated (0.62 g, 1.92 mmol) as a white solid (55%). $[\alpha]_D=-36$ (c=1; $CH_3OH$); $^1$H-NMR ($CD_3OD$): δ 10.05 (bs, 1H, NH), 8.30 (s, 1H), 7.45 (d, 2H, J=7 Hz), 7.30 (d, 2H, J=7 Hz), 3.95 (q, 1H, J=7 Hz), 1.65 (d, 3H, J=7 Hz).

4-Methyl-N-{4-[(1R)-1-(1H-tetrazol-5-yl)ethyl]phenyl}-1,3-oxazol-2-amine (6)

Compound 6 was obtained following the procedure described for the synthesis of 1 starting from the intermediate (2R)-2-{4-[(4-methyl-1,3-thiazol-2-yl)amino]phenyl}propanoic acid (3.5 mmol). Pure 4-methyl-N-{4-[(1R)-1-(1H-tetrazol-5-yl)ethyl]phenyl}-1,3-oxazol-2-amine (6) was isolated (0.59 g, 2.2 mmol) as a white solid (50%). $[\alpha]_D=-19$ (c=1; $CH_3OH$); $^1$H-NMR ($CD_3OD$): δ 9.45 (bs, 1H, NH), 7.95 (s, 1H), 7.45 (d, 2H, J=7 Hz), 7.30 (d, 2H, J=7 Hz), 3.95 (q, 1H, J=7 Hz), 2.20 (s, 3H), 1.65 (d, 3H, J=7 Hz).

5-[(1R)-1-(4-{[4-(trifluoromethyl)-1,3-thiazol-2-yl]amino}phenyl)ethyl]-1H-pyrazol-1-ol (7)

7a) Methyl (4R)-3-oxo-4-(4-{[4-(trifluoromethyl)-1,3-thiazol-2-yl]amino}phenyl) pentanoate To a cooled (0-5° C.) mixture of (2R)-2-(4-{[4-(trifluoromethyl)-1,3-thiazol-2-yl]amino}phenyl)propanoic acid (3 g, 9.5 mmol) in dry $CH_2Cl_2$ (70 ml), DMF (0.073 ml, 0.95 mmol) was added, followed by dropwise addition of oxalyl chloride (0.965 ml, 11.4 mmol). The reaction was stirred at 0° C. for 20 min and then allowed to warm at room temperature and stirred for further 1.5 h. After solvent evaporation (2R)-2-(4-{[4-(trifluoromethyl)-1,3-thiazol-2-yl]amino}phenyl) propanoyl chloride was isolated as a pale yellow oil, pure enough for the next step.

To a cooled solution of recrystallized 2,2-dimethyl-1,3-dioxane-4,6-dione (Meldrum's acid) (1.50 g, 10.45 mmol) in dry $CH_2Cl_2$ (50 ml), dry pyridine (1.8 ml, 22.8 mmol) was added under argon atmosphere over 10 min. period. To the resulting clear solution a solution of (2R)-2-(4-{[4-(trifluoromethyl)-1,3-thiazol-2-yl]amino}phenyl)propanoyl chloride in dry $CH_2Cl_2$ (10 ml) was dripped over a 20 min. period. The resulting reaction mixture was stirred for 1 h at 0° C., then for another hour at room temperature. The reaction mixture was diluted with $CH_2Cl_2$ (15 ml) and poured into 2N HCl (50 ml) containing crushed ice. The organic phase was separated and the aqueous layer extracted with $CH_2Cl_2$ (2×10 ml). The collected organic extracts were combined, washed with 2N HCl (2×10 mL) and with brine (20 ml), dried over anhydrous $Na_2SO_4$ and evaporated to give the acyl Meldrum's intermediate as a pale yellow oil. The crude was refluxed in dry $CH_3OH$ (30 ml) for 2.5 h. After cooling at room temperature and purification by flash chromatography (n-hexane/EtOAc 8:2), methyl (4R)-3-oxo-4-(4-{[4-(trifluoromethyl)-1,3-thiazol-2-yl]amino}phenyl)pentanoate (1.6 g, 4.3 mmol) was isolated as a yellow oil (45%). $^1$H-NMR ($CDCl_3$): δ 9.25 (bs, 1H, NH), 7.40 (d, 2H, J=7 Hz), 7.25 (d, 2H, J=7 Hz), 7.00 (s, 1H), 3.90 (q, 1H, J=7 Hz), 3.75 (s, 3H); 3.40 (s, 2H); 1.55 (d, 3H, J=7 Hz).

7b) N-{4-[(1R)-1-(1H-pyrazol-5-yl)ethyl]phenyl}-4-(trifluoromethyl)-1,3-thiazol-2-amine To a cooled (−78° C.) solution of the ester (1.16 g, 3 mmol) in dry $CH_2Cl_2$ (20 ml) under argon atmosphere DIBAH (1M in hexanes, 3.6 ml) was added dropwise over 15 min via syringe; once the addition was complete, the resulting solution was stirred at −78° C. for 1 h. The reaction was quenched pouring the cold solution into a saturated $NH_4Cl$ solution (10 m). 1M HCl (10 ml) was added and the biphasic mixture was stirred vigorously for 10 min. The layers were separated and the organic one was washed with brine while the aqueous was extracted with $Et_2O$ (2×10 ml). The collected organic extracts were dried over anhydrous $Na_2SO_4$ and concentrated to afford of (4R)-3-oxo-4-(4-{[4-(trifluoromethyl)-1,3-thiazol-2-yl]amino}phenyl)pentanal (728 mg) as a white waxy solid, used without further purification. To a solution of the aldehyde (728 mg) in EtOH/THF (2:1, 15 ml), hydrazine monohydrate (0.495 ml, 10.2 mmol) was added and the mixture refluxed for 30 min. After cooling at room temperature, the mixture was quenched with a saturated $NH_4Cl$ solution and extracted with EtOAc (3×25 ml). The collected organic extracts were washed with brine, dried over anhydrous $Na_2SO_4$ and evaporated under reduced pressure to give N-{4-[(1R)-1-(1H-pyrazol-5-yl)ethyl]phenyl}-4-(trifluoromethyl)-1,3-thiazol-2-amine (421 mg, 1.24 mmol) as a colourless oil (61%). $^1$H-NMR ($CD_3OD$): δ 9.40 (bs, 1H, NH); 7.50 (d, 1H, J=2.5 Hz); 7.40 (d, 2H, J=7 Hz), 7.35 (d, 2H, J=7 Hz), 7.15 (s, 1H), 6.15 (d, 1H, J=2.5 Hz), 3.80 (q, 1H, J=7 Hz), 1.60 (d, 3H, J=7 Hz).

7c) 5-[(1R)-1-(4-{[4-(trifluoromethyl)-1,3-thiazol-2-yl]amino}phenyl)ethyl]-1H-pyrazol-1-ol To a solution of N-{4-[(1R)-1-(1H-pyrazol-5-yl)ethyl]phenyl}-4-(trifluoromethyl)-1,3-thiazol-2-amine (0.421 g, 1.24 mmol) in EtOAc (5 mL) m-CPBA (256 mg, 1.5 mmol) was added and the resulting mixture was stirred at room temperature overnight. The crude was diluted with EtOAc (10 ml), washed with water (2×10 ml) and dried over anhydrous $Na_2SO_4$. After solvent evaporation, the crude was purified by flash chromatography to give the pure 5-[(1R)-1-(4-{[4-(trifluoromethyl)-1,3-thiazol-2-yl]amino}phenyl)ethyl]-1H-pyrazol-1-ol (7) (0.295 g, 0.65 mmol) as a white solid (67%). $[α]_D$=−28 (c=0.82; $CH_3OH$); $^1$H-NMR ($CD_3OD$): δ 9.40 (bs, 1H, NH); 7.55 (d, 1H, J=2.5 Hz); 7.40 (d, 2H, J=7 Hz); 7.35 (d, 2H, J=7 Hz); 7.15 (s, 1H), 6.25 (d, 1H, J=2.4 Hz); 3.80 (q, 1H, J=7 Hz); 1.60 (d, 3H, J=7 Hz).

4-Methyl-5-[(1R)-1-(4-{[4-(trifluoromethyl)-1,3-thiazol-2-yl]amino}phenyl)ethyl]-1H-pyrazol-1-ol (8)

Compound 8 was obtained following the procedure described for the synthesis of 7 starting from the intermediate (2R)-2-(4-{[4-(trifluoromethyl)-1,3-thiazol-2-yl]amino}phenyl)propanoic acid (0.68 mmol) and reacting the corresponding acid chloride with 2,2,5-trimethyl-1,3-dioxane-4,6-dione (0.75 mmol). Pure 4-methyl-5-[(1R)-1-(4-{[4-(trifluoromethyl)-1,3-thiazol-2-yl]amino}phenyl)ethyl]-1H-pyrazol-1-ol (8) was isolated as a white solid (55%). $[α]_D$=−30 (c=1; $CH_3OH$); $^1$H-NMR ($CD_3OD$): δ 9.25 (bs, 1H, NH), 7.40 (d, 2H, J=7 Hz), 7.35 (d, 2H, J=7 Hz), 7.32 (s, 1H), 7.15 (s, 1H), 3.85 (q, 1H, J=7 Hz), 2.05 (s, 3H), 1.60 (d, 3H, J=7 Hz).

5-[(1R)-1-(4-{[4-(trifluoromethyl)-1,3-thiazol-2-yl]amino}phenyl)ethyl]-1H-1,2,3-triazol-1-ol (9)

9a) 2-{4-[(1R)-1-methylprop-2-yn-1-yl]benzyl}-4-(trifluoromethyl)-1,3-thiazole Dimethyl-2-oxopropylphosphonate (0.25 ml, 1.2 mmol) was added to a suspension of $K_2CO_3$ (0.41 g, 3.0 mmol) and p-toluenesulfonylazide (0.24 g, 1.2 mmol) in $CH_3CN$ (15 ml). After stirring for 2 h a solution of (4R)-2-methyl-3-oxo-4-{[4-(trifluoromethyl)-1,3-thiazol-2-yl]amino}phenyl)pentanal (0.34 g, 1.0 mmol) in $CH_3OH$ (5 ml) was added and the resulting mixture was stirred for 8 h at room temperature. The solvents were removed in vacuo and the residue diluted with $Et_2O$ (10 ml), washed with water (2×10 ml) and brine (2×5 ml) and dried over anhydrous $Na_2SO_4$. After solvent evaporation the crude was pulped in n-pentane to give 2-{4-[(1R)-1-methylprop-2-yn-1-yl]benzyl}-4-(trifluoromethyl)-1,3-thiazole (0.22 g, 0.745 mmol) as a colourless oil (75%). $^1$H-NMR ($CDCl_3$): δ 8.68 (bs, 1H, NH); 7.85 (d, 2H, J=7 Hz); 7.55 (d, 2H, J=7 Hz); 7.15 (s, 1H), 3.50 (q, 1H, J=7 Hz); 3.25 (s, 1H), 1.50 (d, 3H, J=7 Hz).

9b) 4-[(1R)-1-(4-{[4-(trifluoromethyl)-1,3-thiazol-2-yl]methyl}phenyl)ethyl]-1H-1,2,3-triazole A cooled (0-5° C.) mixture of 2-{4-[(1R)-1-methylprop-2-yn-1-yl]benzyl}-4-(trifluoromethyl)-1,3-thiazole (0.115 g, 0.4 mmol), p-toluenesulfonylazide (66 mg, 0.33 mmol), 2,6-toluidine (48 mg, 0.4 mmol) and CuI (5% mmol) in $CHCl_3$ (5 ml) was stirred for 12 h. The reaction was quenched by adding a buffer solution (pH=5.4) and the product extracted with $CHCl_3$ (3×5 ml). After solvent evaporation the crude was purified by flash chromatography to give pure 1-(4-methylbenzenesulfonyl)-4-[(1R)-1-(4-{[4-(trifluoromethyl)-1,3-thiazol-2-yl]methyl}phenyl)ethyl]-1H-1,2,3-triazole (0.95 g, 0.20 mmol) as a yellow oil (50%).

9c) N-{4-[(1R)-1-(1H-1,2,3-triazol-5-yl)ethyl]phenyl}-4-(trifluoromethyl)-1,3-thiazol-2-amine The compound was added to a suspension of magnesium turnings (0.20 mmol) in $CH_3OH$ (3 ml) at room temperature and the reaction mixture was stirred for 2 h. By addition of a saturated solution of $NH_4Cl$ (2 ml) the reaction was quenched. The two phases were separated and the organic one washed with water (2×5 ml) and brine (2×5 ml) and dried over anhydrous $Na_2SO_4$. After solvent evaporation the residue was pulped in n-pentane (5 ml) and isolated by filtration to give the pure N-{4-[(1R)-1-(1H-1,2,3-triazol-5-yl)ethyl]phenyl}-4-(trifluoromethyl)-1,3-thiazol-2-amine (0.061 g, 0.18 mmol) as a white solid (90%). $^1$H-NMR ($CD_3OD$): δ 9.40 (bs, 1H, NH), 7.40 (d, 2H, J=7 Hz), 7.35 (d, 2H, J=7 Hz), 7.15 (s, 1H), 7.40 (s, 1H), 3.70 (q, 1H, J=7 Hz), 1.55 (d, 3H, J=7 Hz).

9d) 5-[(1R)-1-(4-{[4-(trifluoromethyl)-1,3-thiazol-2-yl]amino}phenyl)ethyl]-1H-1,2,3-triazol-1-ol To a solution of N-{4-[(1R)-1-(1H-1,2,3-triazol-5-yl)ethyl]phenyl}-4-(trifluoromethyl)-1,3-thiazol-2-amine (0.06 g, 0.18 mmol) in EtOAc (10 ml) m-CPBA (43 mg, 0.25 mmol) was added and the resulting mixture stirred at room temperature overnight. EtOAc (10 ml) was added and the organic layer was washed with water (2×10 ml) and dried over anhydrous $Na_2SO_4$ to give, after solvent evaporation, a crude which, by purification by flash chromatography (EtOAc/$CH_3OH$ 7:3) afforded the pure 5-[(1R)-1-(4-{[4-(trifluoromethyl)-1,3-thiazol-2-yl]amino}phenyl)ethyl]-1H-1,2,3-triazol-1-ol (9) (0.025 g, 0.072 mmol) as a transparent oil (40%). $[\alpha]_D=-19$ (c=1; $CH_3OH$); $^1$H-NMR ($CD_3OD$): δ 9.40 (bs, 1H, NH), 7.40 (d, 2H, J=7 Hz), 7.35 (d, 2H, J=7 Hz), 7.15 (s, 1H), 7.40 (s, 1H), 3.70 (q, 1H, J=7 Hz), 1.55 (d, 3H, J=7 Hz).

5-[(1R)-1-(4-{[4-(trifluoromethyl)-1,3-thiazol-2-yl]amino}phenyl)ethyl]isoxazol-3-ol (10)

To a cooled (−30° C.) solution of the intermediate 7a, methyl (4R)-3-oxo-4-(4-{[4-(trifluoromethyl)-1,3-thiazol-2-yl]amino}phenyl)pentanoate, (372 mg, 1 mmol) in $CH_3OH$ (0.5 ml), a solution of NaOH (42 mg, 1.05 mmol) in $CH_3OH$ (4 ml) was added by dripping. The resulting mixture was stirred for 10 min, then a mixture of hydroxylamine hydrochloride (133 mg, 2 mmol) and NaOH (83 mg, 2 mmol) in $CH_3OH$/water (4 ml/0.5 ml) was added at the same temperature. After stirring for 2 h at −30° C., the reaction mixture was poured into 37% HCl (1.5 ml) and the resulting mixture was heated at 80° C. for 2 h. After cooling at room temperature and solvents evaporation, the crude was diluted with water and extracted with EtOAc (3×10 ml). The combined organic extracts were dried over anhydrous $Na_2SO_4$, evaporated and purified by flash chromatography (n-hexane/EtOAc 8:2; 1% AcOH) to afford pure 5-[(1R)-1-(4-{[4-(trifluoromethyl)-1,3-thiazol-2-yl]amino}phenyl)ethyl]isoxazol-3-ol (10) (202 mg, 0.57 mmol) as a pale yellow solid (57%). $[\alpha]_D=-40$ (c=1.4; $CH_3OH$); $^1$H-NMR ($CDCl_3$): δ 10.70 (bs, 1H, OH), 9.15 (bs, 1H, NH), 7.40 (d, 2H, J=7 Hz), 7.25 (d, 2H, J=7 Hz), 7.00 (s, 1H), 5.70 (s, 1H), 3.80 (q, 1H, J=7 Hz), 1.55 (d, 3H, J=7 Hz).

4-Methyl-5-[(1R)-1-(4-{[5-(trifluoromethyl)-2H-pyrrol-2-yl]amino}phenyl)ethyl]isoxazol-3-ol (11)

The compound was prepared following the same procedure described for the synthesis of 10, but starting from the intermediate (4R)-2-methyl-3-oxo-4-(4-{[4-(trifluoromethyl)-1,3-thiazol-2-yl]amino}phenyl)pentanoate (0.53 mmol) described for the synthesis of 8. Pure 4-methyl-5-[(1R)-1-(4-{[5-(trifluoromethyl)-2H-pyrrol-2-yl]amino}phenyl)ethyl]isoxazol-3-ol (11) (0.11 g, 0.3 mmol) was isolated as a pale yellow solid (57%). $[\alpha]_D=-31$ (c=1.4; $CH_3OH$); $^1$H-NMR ($CDCl_3$): δ 10.70 (bs, 1H, OH), 9.15 (bs, 1H, NH), 7.40 (d, 2H, J=7 Hz), 7.25 (d, 2H, J=7 Hz), 7.00 (s, 1H), 5.70 (s, 1H), 3.80 (q, 1H, J=7 Hz), 2.15 (s, 3H), 1.55 (d, 3H, J=7 Hz).

5-[(1R)-1-(4-{[4-(trifluoromethyl)-1,3-thiazol-2-yl]amino}phenyl)ethyl]isothiazol-3-ol (12)

12a) (4R)-3-oxo-4-(4-{[4-(trifluoromethyl)-1,3-thiazol-2-yl]amino}phenyl)pentanoic acid A solution of methyl (4R)-3-oxo-4-(4-{[4-(trifluoromethyl)-1,3-thiazol-2-yl]amino}phenyl)pentanoate (372 mg, 1 mmol) in AcOH (10 ml) and 37% HCl (1.5 ml) was refluxed for 12 h. After cooling at room temperature and solvents evaporation, the crude product was diluted with $CH_2Cl_2$ (10 ml), washed with water (3×5 ml) and brine (3×5 ml) and dried over anhydrous $Na_2SO_4$. After solvent evaporation the resulting pale yellow oil was pulped overnight in n-hexane. Pure (4R)-3-oxo-4-(4-{[4-(trifluoromethyl)-1,3-thiazol-2-yl]amino}phenyl)pentanoic acid (283 mg, 0.79 mmol) was isolated as a white solid by filtration (79%).

12b) (4R)-3-thioxo-4-(4-{[4-(trifluoromethyl)-1,3-thiazol-2-yl]amino}phenyl) pentanamide To a cooled mixture (0-5° C.) of (4R)-3-oxo-4-(4-{[4-(trifluoromethyl)-1,3-thiazol-2-yl]amino}phenyl)pentanoic acid (283 mg, 0.79 mmol) in $CH_2Cl_2$ (10 ml), CDI (0.128 g, 0.79 mmol) was added. After stirring for 1 h at 0-5° C., gaseous ammonia was bubbled into the mixture for 2 h. The mixture was stirred at room temperature until the complete disappearance of the starting material. A buffer $H_3PO_4/H_2PO_4^-$ solution (pH=2.0, 5 ml) was added and the two phases were separated; the organic one was washed with the same buffer (3×5 ml) and with water (3×5 ml), dried over anhydrous $Na_2SO_4$ and evaporated under vacuum to give a yellow oil, pure enough for the next step. Anhydrous EtOH (5 ml) was saturated with gaseous HCl gas and gaseous $H_2S$, by passing both gases for 30 min each at 0-5° C.; a solution of the intermediate 12a in EtOH (5 ml) was added and gaseous $H_2S$ was bubbled into the solution for further 10 h, keeping the temperature at 0-5° C. After solvents evaporation and purification of the crude by flash chromatography (n-hexane/EtOAc 9:1) (4R)-3-thioxo-4-(4-{[4-(trifluoromethyl)-1,3-thiazol-2-yl]amino}phenyl) pentanamide (150 mg, 0.40 mmol) was isolated as transparent oil (51%).

12c) 5-[(1R)-1-(4-{[4-(trifluoromethyl)-1,3-thiazol-2-yl]amino}phenyl)ethyl]isothiazol-3-ol A solution of iodine (135 mg, 0.53 mmol) in EtOH (5 ml) was added dropwise to a cooled mixture (0-5° C.) of the intermediate 12b (150 mg, 0.40 mmol) and $K_2CO_3$ (212 mg, 1.53 mmol) in EtOH (5 ml). The reaction mixture was stirred for 24 h at room temperature. Water (10 ml) was added and pH adjusted to 3 by 1M HCl. The aqueous layer was extracted with EtOAc (3×10 ml); the collected organic extracts were dried over anhydrous $Na_2SO_4$ and, after solvent evaporation, the purification of the crude by flash chromatography ($CH_2Cl_2$/$CH_3OH$ 95:5) afforded 5-[(1R)-1-(4-{[4-(trifluoromethyl)-1,3-thiazol-2-yl]amino}phenyl)ethyl]isothiazol-3-ol (12) (82 mg, 0.22 mmol) as a white solid (41%). $[\alpha]_D=-31$ (c=1; $CH_3OH$); $^1$H-NMR ($CDCl_3$): δ 10.60 (bs, 1H, OH), 9.15 (bs, 1H, NH), 7.40 (d, 2H, J=7 Hz), 7.25 (d, 2H, J=7 Hz), 7.00 (s, 1H), 5.50 (s, 1H), 3.80 (q, 1H, J=7 Hz), 1.55 (d, 3H, J=7 Hz).

4-[(1R)-1-(4-{[4-(trifluoromethyl)-1,3-thiazol-2-yl]amino}phenyl)ethyl]-1,2,5-oxadiazol-3-ol (13)

13a) (3R)-2-(Hydroxyamino)-3-{4-[(4-(trifluoromethyl)-1,3-thiazol-2-yl)amino]phenyl}butanenitrile To a cooled (0-5° C.) solution of potassium cyanide (0.2 g, 3.66 mmol) in water (15 ml) (2R)-2-(4-{[4-(trifluoromethyl)-1,3-thiazol-2-yl]amino}phenyl)propanal (1.0 g, 3.33 mmol) was added over 30 min. At the same temperature AcOH (3.66 mmol) was added over 30 min and the reaction mixture stirred for 18 h. The solution of the intermediate cyanohydrin was slowly added to a solution of an aqueous solution (2 ml) of NH₄Cl (0.5 g, 9.66 mmol) with hydroxylamine solution (50 wt. % in H₂O; 4.0 mmol) (5 ml). The resulting reaction mixture was stirred at room temperature overnight and then extracted with CH₂Cl₂ (3×15 ml). The organic layer was dried over anhydrous Na₂SO₄ and evaporated under vacuum to give (3R)-2-(hydroxyamino)-3-{4-[(4-(trifluoromethyl)-1,3-thiazol-2-yl)amino]phenyl}butanenitrile (0.74 g, 2.16 mmol) as red-brown oil, used for the next step without further purification. $^1$H-NMR (DMSO-d₆): δ 8.25 (bs, 1H, OH), 7.40 (d, 2H, J=7 Hz), 7.25 (d, 2H, J=7 Hz), 7.05 (s, 1H), 5.15 (s, 1H), 3.90 (q, 1H, J=7 Hz), 1.75 (d, 3H, J=7 Hz).

13b) 4-[(1R)-1-{4-[(4-(trifluoromethyl)-1,3-thiazol-2-yl)amino]phenyl}ethyl]-1,2,5-oxadiazol-3-amine A mixture of intermediate 13a (0.738 gr, 2.16 mmol), hydroxylamine hydrochloride (83 mg, 2.50 mmol) and sodium acetate (410 mg, 5 mmol) in EtOH (15 ml) was refluxed for 4 h. After cooling, the precipitate was collected by filtration and dried. The precipitated α-oximido-acetamidoxime sodium acetate derivative was refluxed with excess PCl₅ in dry Et₂O (15 ml) for 6 h. After cooling at room temperature the reaction was quenched with a buffered solution at pH 8.2 (10 ml) and the two phases separated. The aqueous layer was extracted with Et₂O (2×10 ml) and the collected organic phases were dried over anhydrous Na₂SO₄ and evaporated under vacuum to give 4-[(1R)-1-{4-[(4-(trifluoromethyl)-1,3-thiazol-2-yl)amino]phenyl}ethyl]-1,2,5-oxadiazol-3-amine (0.57 g, 1.62 mmol) as a white solid (75%). $^1$H-NMR (DMSO-d₆): δ 8.25 (bs, 1H, NH), 7.40 (d, 2H, J=7 Hz), 7.25 (d, 2H, J=7 Hz), 7.05 (s, 1H), 5.15 (bs, 2H, NH₂), 3.90 (q, 1H, J=7 Hz), 1.75 (d, 3H, J=7 Hz).

13c) 4-[(1R)-1-(4-{[4-(trifluoromethyl)-1,3-thiazol-2-yl]amino}phenyl)ethyl]-1,2,5-oxadiazol-3-ol To a cooled solution of 4-[(1R)-1-{4-[(4-(trifluoromethyl)-1,3-thiazol-2-yl)amino]phenyl}ethyl]-1,2,5-oxadiazol-3-amine (0.2 g, 0.56 mmol) in AcOH (5 ml) and 37% HCl (3 ml), a solution of sodium nitrite (44 mg, 0.845 mmol) in water (3 ml) was added dropwise. The resulting reaction mixture was stirred for 30 min, then conc. H₂SO₄ (0.5 ml) was added and the reaction quenched with a saturated solution of NH₄Cl (10 ml); the resulting mixture was extracted with Et₂O (3×10 ml) and the collected organic extracts were evaporated under vacuum; the crude was purified by flash chromatography to afford pure 4-[(1R)-1-(4-{[4-(trifluoromethyl)-1,3-thiazol-2-yl]amino}phenyl)ethyl]-1,2,5-oxadiazol-3-ol (13) (0.17 g, 0.48 mmol) as a white solid (85%). [α]$_D$=−51 (c=1; CH₃OH); $^1$H-NMR (DMSO-d₆): δ 8.25 (bs, 1H, NH), 7.40 (d, 2H, J=7 Hz), 7.25 (d, 2H, J=7 Hz), 7.05 (s, 1H), 3.90 (q, 1H, J=7 Hz), 1.75 (d, 3H, J=7 Hz).

4-[(1R)-1-(4-{[4-(trifluoromethyl)-1,3-thiazol-2-yl]amino}phenyl)ethyl]-1,2,5-thiadiazol-3-ol (14)

14a) (3R)-2-amino-3-{4-[(4-(trifluoromethyl)-1,3-thiazol-2-yl)amino]phenyl}butanenitrile To a cooled (0-5° C.) solution of potassium cyanide (0.2 g, 3.66 mmol) in water (15 ml) (2R)-2-(4-{[4-(trifluoromethyl)-1,3-thiazol-2-yl]amino}phenyl)propanal (1.0 g, 3.33 mmol) (prepared according the procedure described for intermediate 7b and starting from the corresponding propanoate) was added over 30 min. At the same temperature AcOH (3.66 mmol) was dripped and the reaction mixture stirred for 18 h. The solution of the intermediate cyanohydrin was slowly added to another solution of NH₄Cl (0.5 g, 9.66 mmol) in NH₄OH (14N in H₂O; 4.0 mmol) (5 ml). The resulting reaction mixture was stirred at room temperature for 18 h and then extracted with CH₂Cl₂ (3×15 ml). The organic layer was dried over anhydrous Na₂SO₄ and evaporated under vacuum to give (3R)-2-amino-3-{4-[(4-(trifluoromethyl)-1,3-thiazol-2-yl)amino]phenyl}butanenitrile (0.705 g, 2.16 mmol) as red oil, used for the next step without further purification. $^1$H-NMR (DMSO-d₆): δ 9.25 (bs, 1H, NH), 7.40 (d, 2H, J=7 Hz), 7.25 (d, 2H, J=7 Hz), 7.00 (s, 1H), 5.00 (s, 1H), 3.90 (q, 1H, J=7 Hz), 2.35 (bs, 2H), 1.75 (d, 3H, J=7 Hz).

14b) N-{4-[(1R)-1-(4-chloro-1,2,5-thiadiazol-3-yl)ethyl]phenyl}-4-(trifluoromethyl)-1,3-thiazol-2-amine To a cooled (5-10° C.) solution of sulfur monochloride (0.35 ml, 4.32 mmol) in DMF (15 ml), a solution of intermediate 14a (0.7 g, 2.16 mmol) in DMF (5 ml) was added over 1 h. The reaction mixture was stirred for 1 h; iced water (30 ml) was added to keep the temperature below 20° C. and to allow the precipitation of sulphur. The mixture was filtrated and the mother liquors diluted with a buffer solution (pH 8.5, 50 ml). The aqueous layer was extracted with CH₂Cl₂ (2×10 ml) and the collected organic extracts evaporated to give a crude that, after purification by crystallization from n-heptane, afforded the pure N-{4-[(1R)-1-(4-chloro-1,2,5-thiadiazol-3-yl)ethyl]phenyl}-4-(trifluoromethyl)-1,3-thiazol-2-amine (1.09 g, 2.80 mmol) as yellow solid (65%). $^1$H-NMR (CDCl₃): δ 9.25 (bs, 1H, NH), 7.40 (d, 2H, J=7 Hz), 7.25 (d, 2H, J=7 Hz), 7.00 (s, 1H), 3.85 (q, 1H, J=7 Hz) 1.75 (d, 3H, J=7 Hz).

14c) 4-[(1R)-1-(4-{[4-(trifluoromethyl)-1,3-thiazol-2-yl]amino}phenyl)ethyl]-1,2,5-thiadiazol-3-ol Intermediate 14b (1.09 g, 2.80 mmol) was dissolved in a solution of NaOH (0.11 g, 2.75 mmol) in CH₃OH (10 ml). The reaction mixture was stirred for 1 h at 50° C. and then quenched with a saturated solution of NH₄Cl (10 ml); the aqueous layer was extracted with CH₂Cl₂ (2×10 ml) and the combined organic phases, after drying over anhydrous Na₂SO₄, were evaporated under vacuum and crystallized from n-heptane to give the pure 4-[(1R)-1-(4-{[4-(trifluoromethyl)-1,3-thiazol-2-yl]amino}phenyl)ethyl]-1,2,5-thiadiazol-3-ol (14) (0.625 g, 1.68 mmol) as a white solid (60%). [α]$_D$=−33 (c=1; CH₃OH); $^1$H-NMR (CDCl₃): δ 9.25 (bs, 1H, NH), 8.35 (bs, 1H, OH), 7.40 (d, 2H, J=7 Hz), 7.25 (d, 2H, J=7 Hz), 7.00 (s, 1H), 3.85 (q, 1H, J=7 Hz) 1.75 (d, 3H, J=7 Hz).

5-[(1R)-1-(4-{[4-(trifluoromethyl)-1,3-thiazol-2-yl]amino}phenyl)ethyl]-1H-1,2,4-triazol-1-ol (15)

15a) (2R)-2-(4-{[4-(trifluoromethyl)-1,3-thiazol-2-yl]amino}phenyl)propan imidamide Gas HCl was bubbled for 5 h into a solution of intermediate 1b (0.64 g, 2.15 mmol) in CH₃OH/Et₂O (1:1, 20 ml) and then the mixture was stirred overnight at room temperature. The solvent was evaporated and the crude, after dissolution in CH₃OH (10 ml), was treated with gas NH₃ up to saturation of the solution. The resulting mixture was stirred at room temperature overnight. After evaporation, the residue was dissolved in CH₂Cl₂ (10 ml) and washed with 1M HCl (3×5 ml). The collected aqueous phases were extracted back with EtOAc (3×10 ml). The combined organic extracts were dried over anhydrous Na₂SO₄ and evaporated under vacuum to give pure (2R)-2-(4-{[4-(trifluoromethyl)-1,3-thiazol-2-yl]amino}phenyl) propanimidamide (0.4 g, 1.29 mmol) as yellow solid (60%). $^1$H-NMR (CD$_3$OD): δ 9.45 (bs, 1H, NH), 9.10 (s, 1H), 8.80 (s, 2H), 7.45 (d, 2H, J=7 Hz), 7.30 (d, 2H, J=7 Hz), 7.15 (s, 1H), 3.95 (q, 1H, J=7 Hz), 1.55 (d, 3H, J=7 Hz).

15b) N-{4-[(1R)-1-(1H-1,2,4-triazol-5-yl)ethyl]phenyl}-4-(trifluoromethyl)-1,3-thiazol-2-amine To a solution of intermediate 15a (0.4 g, 1.29 mmol) in EtOH (5 ml) formylhydrazine (95 mg, 1.55 mmol) was added and the mixture refluxed for 48 h. After cooling at room temperature, the solvent was distilled off and the crude dissolved in CH$_2$Cl$_2$ (10 ml), washed with 1M HCl (2×5 ml), dried over anhydrous Na$_2$SO$_4$ and evaporated under vacuum to give a crude that, after purification by flash chromatography, afforded the pure N-{4-[(1R)-1-(1H-1,2,4-triazol-5-yl)ethyl]phenyl}-4-(trifluoromethyl)-1,3-thiazol-2-amine (0.22 mg, 0.645 mmol) as yellow (42%). $^1$H-NMR (CD$_3$OD): δ 9.45 (bs, 1H, NH), 7.45 (d, 2H, J=7 Hz), 7.30 (d, 2H, J=7 Hz), 7.15 (s, 1H), 3.95 (q, 1H, J=7 Hz), 1.55 (d, 3H, J=7 Hz).

15c) 5-[(1R)-1-(4-{[4-(trifluoromethyl)-1,3-thiazol-2-yl]amino}phenyl)ethyl]-1H-1,2,4-triazol-1-ol To a solution of intermediate 15b (0.21 g, 0.62 mmol) in EtOAc (5 ml), m-CPBA was added (0.17 g, 0.97 mmol) and the resulting mixture was stirred at room temperature overnight. The reaction mixture was washed with water (2×10 ml) and anhydrous Na$_2$SO$_4$ and evaporated under vacuum to give a crude that, after purification by flash chromatography, afforded the pure 5-[(1R)-1-(4-{[4-(trifluoromethyl)-1,3-thiazol-2-yl]amino}phenyl)ethyl]-1H-1,2,4-triazol-1-ol (15) as a white solid (67%). [α]$_D$=−35 (c=0.82; CH$_3$OH); $^1$H-NMR (CD$_3$OD): δ 9.40 (bs, 1H, NH); 7.55 (d, 1H, J=2.5 Hz); 7.40 (d, 2H, J=7 Hz); 7.35 (d, 2H, J=7 Hz); 7.15 (s, 1H), 6.25 (d, 1H, J=2.4 Hz); 3.80 (q, 1H, J=7 Hz); 1.60 (d, 3H, J=7 Hz).

EXAMPLE 3

Biological Assays

3a) Inhibition of C5a-Induced Chemotactic Activity

The compounds prepared in Example 2 were evaluated in vitro for their ability to inhibit chemotaxis of polymorphonucleate leukocytes (hereinafter referred to as PMNs) and monocytes induced by the fractions of the complement C5a and C5a-desArg. For this purpose, to isolate the PMNs from heparinized human blood, taken from healthy adult volunteers, mononucleates were removed by means of sedimentation on dextran (according to the procedure disclosed by W. J. Ming et al., J. Immunol., 138, 1469, 1987) and red blood cells by a hypotonic solution. The cell vitality was calculated by exclusion with Trypan blue, whilst the ratio of the circulating polymorphonucleates was estimated on the cytocentrifugate after staining with Diff Quick.

Human recombinant fractions C5a and C5a-desArg (Sigma) were used as stimulating agents in the chemotaxis experiments, giving practically identical results.

The lyophilized C5a was dissolved in a volume of HBSS containing 0.2% bovin serum albumin BSA so thus to obtain a stock solution having a concentration of 10$^{-5}$ M to be diluted in HBSS to a concentration of 10$^{-9}$ M, for the chemotaxis assays.

In the chemotaxis experiments, the PMNs were incubated with the compounds of the invention of formula (I) for 15' at 37° C. in an atmosphere containing 5% CO$_2$. The chemotactic activity of the C5a was evaluated on human circulating polymorphonucleates (PMNs) resuspended in HBSS at a concentration of 1.5×10$^6$ PMNs per ml. During the chemotaxis assay (according to W. Falket et al., J. Immunol. Methods, 33, 239, 1980) PVP-free filters with a porosity of 5 μm and microchambers suitable for replication were used.

The compounds of Example 2 were evaluated at a concentration ranging between 10$^{-7}$ and 10$^{-10}$ M; for this purpose they were added, at the same concentration, both to the lower pores and the upper pores of the microchamber. The wells in the lower part contain the solution of C5a or the simple carrier, those in the upper part contain the suspension of PMNs.

Inhibition of C5a-induced chemotactic activity by the individual compounds was evaluated by incubating the microchamber for the chemotaxis for 60 min at 37° C. in an atmosphere containing 5% CO$_2$.

Evaluation of the ability of the tested compounds to inhibit C5a-induced chemotaxis of human monocytes was carried out according to the method disclosed by Van Damme J. et al. (Eur. J. Immunol., 19, 2367, 1989) Inhibition of C5a-induced chemotactic activity by the individual compounds towards human monocytes was evaluated at a concentration ranging between 10$^{-7}$ and 10$^{-10}$M by incubating the microchamber for the chemotaxis for 120 min. at 37° C. in an atmosphere containing 5% CO$_2$.

The inhibition data of the chemotaxis of PMNs (concentration 10$^{-8}$M) observed are reported in Table 1.

3b) Inhibition of the Production of PGE$_2$

The compounds prepared in Example 2 were evaluated ex vivo in the blood in toto according a procedure disclosed by Patrignani et al. (J. Pharmacol. Exper. Ther., 271, 1705, 1994). In all cases, the compounds of formula (I) do not interfere with the production of PGE$_2$ induced in murine macrophages by lipopolysaccharides stimulation (LPS, 1 μg/ml) at a concentration ranging between 10$^{-5}$ and 10$^{-7}$ M. Inhibition of the production of PGE$_2$ is mostly at the limit of statistical significance, and generally below 15-20% of the basal value.

TABLE 1

| | Activity on PMNs C5a induced chemotaxis | |
| --- | --- | --- |
| Name | Structure | C5a (% inhibition at 10$^{-8}$ M) |
| N-{4-[(1R)-1-(1H-tetrazol-5-yl)ethyl]phenyl}-4-(trifluoromethyl)-1,3-thiazol-2-amine (1) | | 60 ± 1 |

TABLE 1-continued

Activity on PMNs C5a induced chemotaxis

| Name | Structure | C5a (% inhibition at $10^{-8}$ M) |
|---|---|---|
| 4-methyl-N-{4-[(1R)-1-(1H-tetrazol-5-yl)ethyl]phenyl}-1,3-thiazol-2-amine (2) | 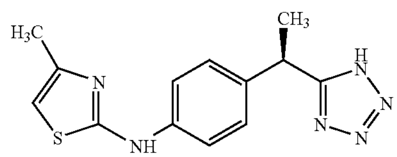 | 45 ± 3 |
| 4-tert-butyl-N-{4-[(1R)-1-(1H-tetrazol-5-yl)ethyl]phenyl}-1,3-thiazol-2-amine (3) | 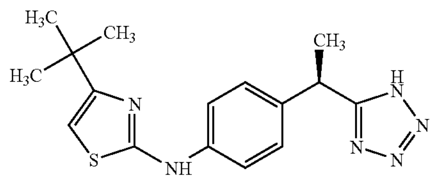 | 42 ± 8 |
| N-{4-[(1R)-1-(1H-tetrazol-5-yl)ethyl]phenyl}-1,3-thiazol-2-amine (4) | 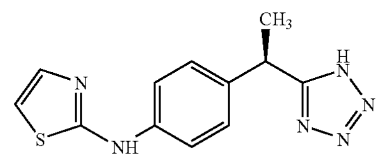 | 39 ± 3 |
| N-{4-[(1R)-1-(1H-tetrazol-5-yl)ethyl]phenyl}-4-(trifluoromethyl)-1,3-oxazol-2-amine (5) | 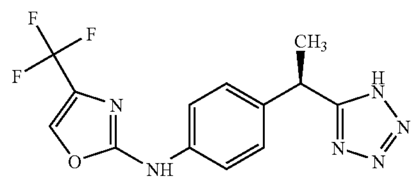 | 55 ± 1 |
| 4-methyl-N-{4-[(1R)-1-(1H-tetrazol-5-yl)ethyl]phenyl}-1,3-oxazol-2-amine (6) | 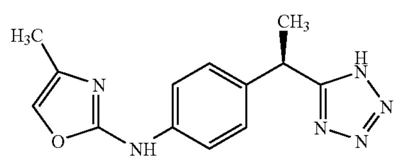 | 51 ± 7 |
| 5-[(1R)-1-(4-{[4-(trifluoromethyl)-1,3-thiazol-2-yl]amino}phenyl)ethyl]-1H-pyrazol-1-ol (7) | 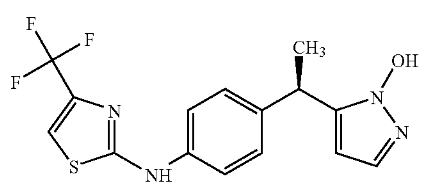 | 38 ± 6 |
| 4-methyl-5-[(1R)-1-(4-{[4-(trifluoromethyl)-1,3-thiazol-2-yl]amino}phenyl)ethyl]-1H-pyrazol-1-ol (8) | | 48 ± 5 |
| 5-[(1R)-1-(4-{[4-(trifluoromethyl)-1,3-thiazol-2-yl]amino}phenyl)ethyl]-1H-1,2,3-triazol-1-ol (9) | 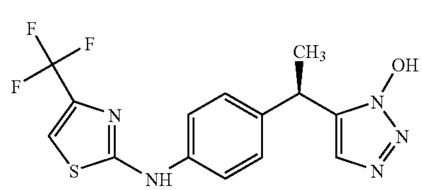 | 44 ± 1 |

TABLE 1-continued

Activity on PMNs C5a induced chemotaxis

| Name | Structure | C5a (% inhibition at $10^{-8}$ M) |
|---|---|---|
| 5-[(1R)-1-(4-{[4-(trifluoromethyl)-1,3-thiazol-2-yl]amino}phenyl)ethyl]isoxazol-3-ol (10) | 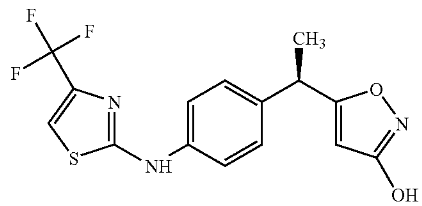 | 56 ± 1 |
| 4-methyl-5-[(1R)-1-(4-{[4-(trifluoromethyl)-1,3-thiazol-2-yl]amino}phenyl)ethyl]isoxazol-3-ol (11) | 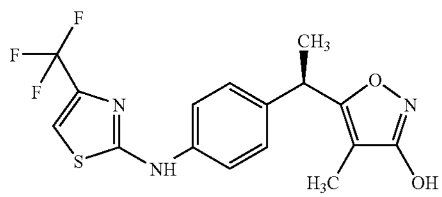 | 45 ± 4 |
| 5-[(1R)-1-(4-{[4-(trifluoromethyl)-1,3-thiazol-2-yl]amino}phenyl)ethyl]isothiazol-3-ol (12) | 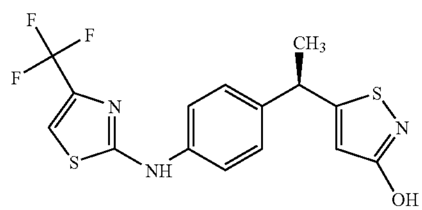 | 45 ± 3 |
| 4-[(1R)-1-(4-{[4-(trifluoromethyl)-1,3-thiazol-2-yl]amino}phenyl)ethyl]-1,2,5-oxadiazol-3-ol (13) | 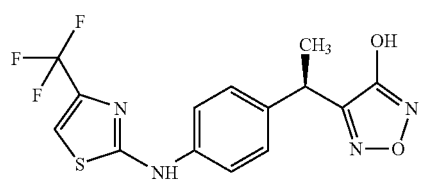 | 51 ± 4 |
| 4-[(1R)-1-(4-{[4-(trifluoromethyl)-1,3-thiazol-2-yl]amino}phenyl)ethyl]-1,2,5-thiadiazol-3-ol (14) | 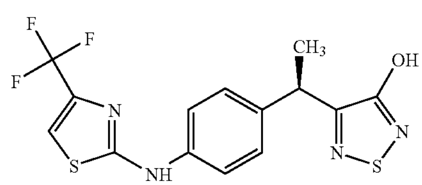 | 60 ± 9 |
| 5-[(1R)-1-(4-{[4-(trifluoromethyl)-1,3-thiazol-2-yl]amino}phenyl)ethyl]-1H-1,2,4-triazol-1-ol (15) | 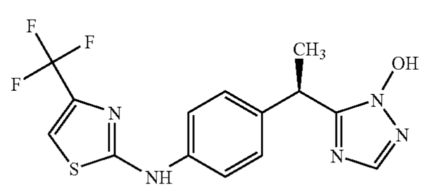 | 43 ± 1 |

The invention claimed is:
1. (R)-4-(heteroaryl)phenylpropionic compounds of formula (I):

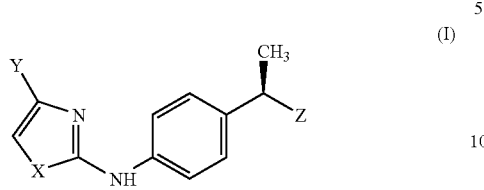

and pharmaceutically acceptable salts thereof, wherein
X is a heteroatom selected from
S, O and N
Y is H or a residue selected from the group consisting of:
halogen, linear or branched $C_1$-$C_4$-alkyl, $C_2$-$C_4$-alkenyl, $C_1$-$C_4$-alkoxy, hydroxy, —COOH, $C_1$-$C_4$-acyloxy, phenoxy, cyano, nitro, —$NR_2$, $C_1$-$C_4$-acylamino, halo-$C_1$-$C_3$-alkyl, benzoyl, linear or branched $C_1$-$C_8$-alkanesulfonate, linear or branched $C_1$-$C_8$-alkanesulfonamides, linear or branched $C_1$-$C_8$-alkyl sulfonylmethyl;
Z is an heteroaryl ring selected from the group consisting of:
unsubstituted tetrazole and
triazole, pyrazole, oxazole, thiazole, isooxazole, isothiazole, thiadiazole and oxadiazole substituted by one hydroxy group and optionally further substituted by one or more goups selected from the group consisting of halogen, linear or branched $C_1$-$C_4$-alkyl, $C_2$-$C_4$-alkenyl, $C_1$-$C_4$-alkylamino, $C_1$-$C_4$-alkoxy, $C_1$-$C_4$-alkylthio, $C_1$-$C_4$-acyloxy, cyano, nitro, $NH_2$, $C_1$-$C_4$-acylamino, halo-$C_1$-$C_3$-alkyl, halo-$C_1$-$C_3$-alkoxy, linear or branched $C_1$-$C_8$-alkanesulfonate and linear or branched $C_1$-$C_8$-alkanesulfonamides.
2. Compounds according to claim 1 wherein:
X is a heteroatom selected from
S and O
Y is H or a residue selected from the group consisting of:
halogen, linear or branched $C_1$-$C_4$-alkyl and halo-$C_1$-$C_3$-alkyl;
Z is an heteroaryl ring selected from the group consisting of:
unsubstituted tetrazole and
triazole, pyrazole, isooxazole, isothiazole, thiadiazole and oxadiazole substituted by one hydroxy group and optionally further substituted by one or more groups selected from the group consisting of halogen, linear or branched $C_1$-$C_4$-alkyl, $C_1$-$C_4$-alkylthio and halo-$C_1$-$C_3$-alkyl.
3. Compounds according to claim 1, wherein:
Y is H or a residue selected from the group consisting of trifluoromethyl, chlorine, methyl and tert-butyl.
4. Compounds according to claim 1, wherein
said triazole, pyrazole, isooxazole, isothiazole, thiadiazole or oxadiazole ring is substituted by one hydroxy group and optionally further substituted by one or more groups selected from the group consisting of methyl, trifluoromethyl and chlorine.
5. Compounds according to claim 1, selected from the group consisting of:
N-{4-[(1R)-1-(1H-tetrazol-5-yl)ethyl]phenyl}-4-(trifluoromethyl)-1,3-thiazol-2-amine;
4-methyl-N-{4-[(1R)-1-(1H-tetrazol-5-yl)ethyl]phenyl}-1,3-thiazol-2-amine;
4-tert-butyl-N-{4-[(1R)-1-(1H-tetrazol-5-yl)ethyl]phenyl}-1,3-thiazol-2-amine;
N-{4-[(1R)-1-(1H-tetrazol-5-yl)ethyl]phenyl}-1,3-thiazol-2-amine;
N-{4-[(1R)-1-(1H-tetrazol-5-yl)ethyl]phenyl}-4-(trifluoromethyl)-1,3-oxazol-2-amine;
4-methyl-N-{4-[(1R)-1-(1H-tetrazol-5-yl)ethyl]phenyl}-1,3-oxazol-2-amine;
5-[(1R)-1-(4-{[4-(trifluoromethyl)-1,3-thiazol-2-yl]amino}phenyl)ethyl]-1H-pyrazol-1-ol;
4-methyl-5-[(1R)-1-(4-{[4-(trifluoromethyl)-1,3-thiazol-2-yl]amino}phenyl)ethyl]-1H-pyrazol-1-ol;
5-[(1R)-1-(4-{[4-(trifluoromethyl)-1,3-thiazol-2-yl]amino}phenyl)ethyl]-1H-1,2,3-triazol-1-ol;
5-[(1R)-1-(4-{[4-(trifluoromethyl)-1,3-thiazol-2-yl]amino}phenyl)ethyl]isoxazol-3-ol;
4-methyl-5-[(1R)-1-(4-{[4-(trifluoromethyl)-1,3-thiazol-2-yl]amino}phenyl)ethyl]isoxazol-3-ol;
5-[(1R)-1-(4-{[4-(trifluoromethyl)-1,3-thiazol-2-yl]amino}phenyl)ethyl]isothiazol-3-ol;
4-[(1R)-1-(4-{[4-(trifluoromethyl)-1,3-thiazol-2-yl]amino}phenyl)ethyl]-1,2,5-oxadiazol-3-ol;
4-[(1R)-1-(4-{[4-(trifluoromethyl)-1,3-thiazol-2-yl]amino}phenyl)ethyl]-1,2,5-thiadiazol-3-ol;
5-[(1R)-1-(4-{[4-(trifluoromethyl)-1,3-thiazol-2-yl]amino}phenyl)ethyl]-1H-1,2,4-triazol-1-ol.
6. A pharmaceutical composition comprising a therapeutically effective amount of the compound according to claim 1 in combination with at least one pharmaceutically acceptable excipient and/or a diluent.
7. A method for the treatment of diseases involving C5a induced human PMNs chemotaxis, wherein said diseases are selected from the group consisting of: autoimmune hemolytic anemia (AIHA), psoriasis, bullous pemphigoid, rheumatoid arthritis, ulcerative colitis, acute respiratory distress syndrome, idiopathic fibrosis glomerulonephritis, injury caused by ischemia and reperfusion, comprising administering to a patient in need thereof the pharmaceutical composition according to claim 6.
8. A method for prevention of injury caused By ischemia and reperfusion, comprising administering to a patient in need thereof the pharmaceutical composition according to claim 6.
9. Process for the preparation of compounds of claim 1, wherein Z is tetrazole, comprising the reaction of compound of formula (II),

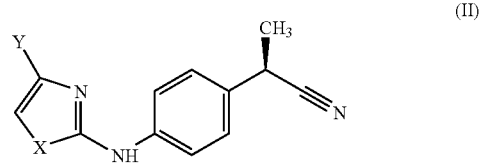

wherein X and Y have the same meaning as defined in claim 1, with trimethylsilylazide, affording the corresponding tetrazoles of formula (I).
10. A method for reducing the risk of injury caused by ischemia and reperfusion, comprising administering to a patient in need thereof the pharmaceutical composition according to claim 6.

* * * * *